US009333122B2

(12) United States Patent
Takino et al.

(10) Patent No.: US 9,333,122 B2
(45) Date of Patent: May 10, 2016

(54) DISPOSABLE WEARING ARTICLE

(75) Inventors: Shunsuke Takino, Kagawa (JP); Hiroki Mori, Kagawa (JP)

(73) Assignee: Unicharm Corporation, Ehime (JP)

( * ) Notice: Subject to any disclaimer, the term of this patent is extended or adjusted under 35 U.S.C. 154(b) by 925 days.

(21) Appl. No.: 13/508,131

(22) PCT Filed: Nov. 5, 2010

(86) PCT No.: PCT/JP2010/006507
§ 371 (c)(1),
(2), (4) Date: May 4, 2012

(87) PCT Pub. No.: WO2011/055546
PCT Pub. Date: May 12, 2011

(65) Prior Publication Data
US 2012/0215191 A1    Aug. 23, 2012

(30) Foreign Application Priority Data
Nov. 6, 2009  (JP) ................................. 2009-254547

(51) Int. Cl.
*A61F 13/15*    (2006.01)
*A61F 13/496*   (2006.01)
*A61F 13/49*    (2006.01)

(52) U.S. Cl.
CPC ......... *A61F 13/496* (2013.01); *A61F 13/15593* (2013.01); *A61F 13/49011* (2013.01)

(58) Field of Classification Search
CPC .................... A61F 13/49058; A61F 13/49061
USPC ........................... 604/385.3, 385.02, 385.201
See application file for complete search history.

(56) References Cited

U.S. PATENT DOCUMENTS

| 2005/0177124 A1* | 8/2005 | Kondo ................... A61F 13/42 |
| | | 604/385.29 |
| 2007/0208316 A1* | 9/2007 | Nakahata et al. ........ 604/385.02 |

(Continued)

FOREIGN PATENT DOCUMENTS

| JP | 03-205053   A | 6/1991 |
| JP | 2004-305772 A | 11/2004 |
| JP | 2008-036198 A | 2/2008 |
| JP | 2008-043674 A | 2/2008 |
| JP | 2008-178682 A | 8/2008 |

(Continued)

OTHER PUBLICATIONS

International Search Report from corresponding PCT application No. PCT/JP2010/006507 dated Jan. 25, 2011 (2 pgs).

*Primary Examiner* — Susan Su
(74) *Attorney, Agent, or Firm* — Brinks Gilson & Lione

(57) ABSTRACT

A disposable wearing article including a buttocks-covering section having tensile force sufficient to prevent this section from lifting and/or quirking during use of the wearing article and being free from anxiety that the buttocks-covering section might irritate the wearer's skin even if this section comes in contact with the wearer's skin. In this diaper, a rear waist region includes an inner sheet lying on a skin-facing side, an outer sheet lying on a non-skin-facing side, a rear waist main section facing a front waist region and a buttocks-covering section located below the rear waist main section wherein the buttocks-covering section is provided with a plurality of buttocks-covering section elastic elements in the form of strands extending in a transverse direction at a given distance one from another in a longitudinal direction and, in the buttocks-covering section, the inner sheet and the outer sheet are bonded to each other by adhesive applied to peripheral surfaces of the respective buttocks-covering section elastic elements.

9 Claims, 8 Drawing Sheets

(56) References Cited

U.S. PATENT DOCUMENTS

| | | | | |
|---|---|---|---|---|
| 2009/0326504 | A1* | 12/2009 | Kaneda | A61F 13/49011 604/385.23 |
| 2010/0280472 | A1* | 11/2010 | Takeuchi | A61F 13/42 604/367 |
| 2011/0144611 | A1* | 6/2011 | Saito | A61F 13/49011 604/385.14 |
| 2012/0046632 | A1* | 2/2012 | Malowaniec | A61F 13/49011 604/385.24 |

FOREIGN PATENT DOCUMENTS

| | | | |
|---|---|---|---|
| JP | 2008-228835 | A | 10/2008 |
| JP | 2009-118986 | A | 6/2009 |
| JP | 2009-160129 | A | 7/2009 |
| JP | 2007/0208316 | | 8/2009 |
| JP | 2010/0280472 | | 9/2009 |
| JP | 2009207564 | A * | 9/2009 |
| WO | WO 2007/138821 | A1 | 12/2007 |
| WO | WO 2009/084643 | A1 | 7/2009 |

\* cited by examiner (a)

(b)

DISPOSABLE WEARING ARTICLE

RELATED APPLICATION

This application is a 35 U.S.C. §371 national phase filing of International Patent Application No. PCT/JP2010/006507, filed Nov. 5, 2010, through which and to which priority is claimed under 35 U.S.C. §119 to Japanese Patent Application No. 2009-254547, filed Nov. 6, 2009.

TECHNICAL FIELD

The present invention relates to disposable wearing articles and more particularly to disposable wearing articles such as disposable diapers each having a buttocks-covering section adapted to cover the wearer's buttocks, disposable toilet-training pants, disposable incontinent pants or disposable menstruation napkins.

RELATED ART

Disposable wearing articles each having a section adapted to cover the wearer's buttocks have been known. For example, PATENT DOCUMENT 1 (JP 2008-178682 A) discloses a wearing article having front and rear waist regions, a crotch region, elastic waist members respectively forming the front and rear waist regions and a liquid-absorbent chassis bonded to the inner surface of the elastic waist members wherein there is additionally provided a buttocks-covering section extending from the rear waist region toward the crotch region.

The wearing article according to the invention disclosed in PATENT DOCUMENT 1 (JP 2008-178682 A) includes the buttocks-covering section extending downward from the rear waist region to improve appearance as well as feeling to wear. The buttocks-covering section is provided with a plurality of elastic elements extending in the transverse direction of the wearing article so that the buttocks-covering section is prevented from lifting and/or quirking.

However, in such wearing article, the inner sheet and the outer sheet cooperating to form a part of the buttocks-covering section are bonded to each other by adhesive applied over the entire area of the inner surfaces of these inner and outer sheets. In consequence, stiffness of the sheets as a whole becomes relatively high and bonded region along the peripheral edge of the buttocks-covering section may irritate the wearer's skin when the bonded region comes in contact with the wearer's skin. Particularly, the lower end section extending downward from the both side edges of the rear waist region are angulated and these angulated regions might irritate the wearer's skin.

CITATION LIST

Patent Document

[PATENT DOCUMENT 1] JP 2008-178682 A

SUMMARY

A disposable wearing article in accordance with one or more embodiments of the present invention has a longitudinal direction, a transverse direction orthogonal to the longitudinal direction, a skin-facing side, a non-skin-facing side, a front waist region, a rear waist region, a crotch region extending between the front and rear waist regions, and comprising elastic waist panels defining the front and rear waist regions and a liquid-absorbent structure attached to an inner surface of the elastic waist panel to define the crotch region.

In the wearing article, the rear waist region comprises an inner sheet lying on the skin-facing side, an outer sheet lying on the non-skin-facing side, a rear waist main section and a buttocks-covering section lying below the rear waist main section; the buttocks-covering section includes a plurality of buttocks-covering section elastic elements arranged thereon to extend in the transverse direction at constant intervals in the longitudinal direction; and, in the buttocks-covering section, the inner sheet and the outer sheet are bonded to each other by adhesive applied to peripheral surfaces of the respective buttocks-covering section elastic elements.

DETAILED DESCRIPTION

First Embodiment

Figure 1:
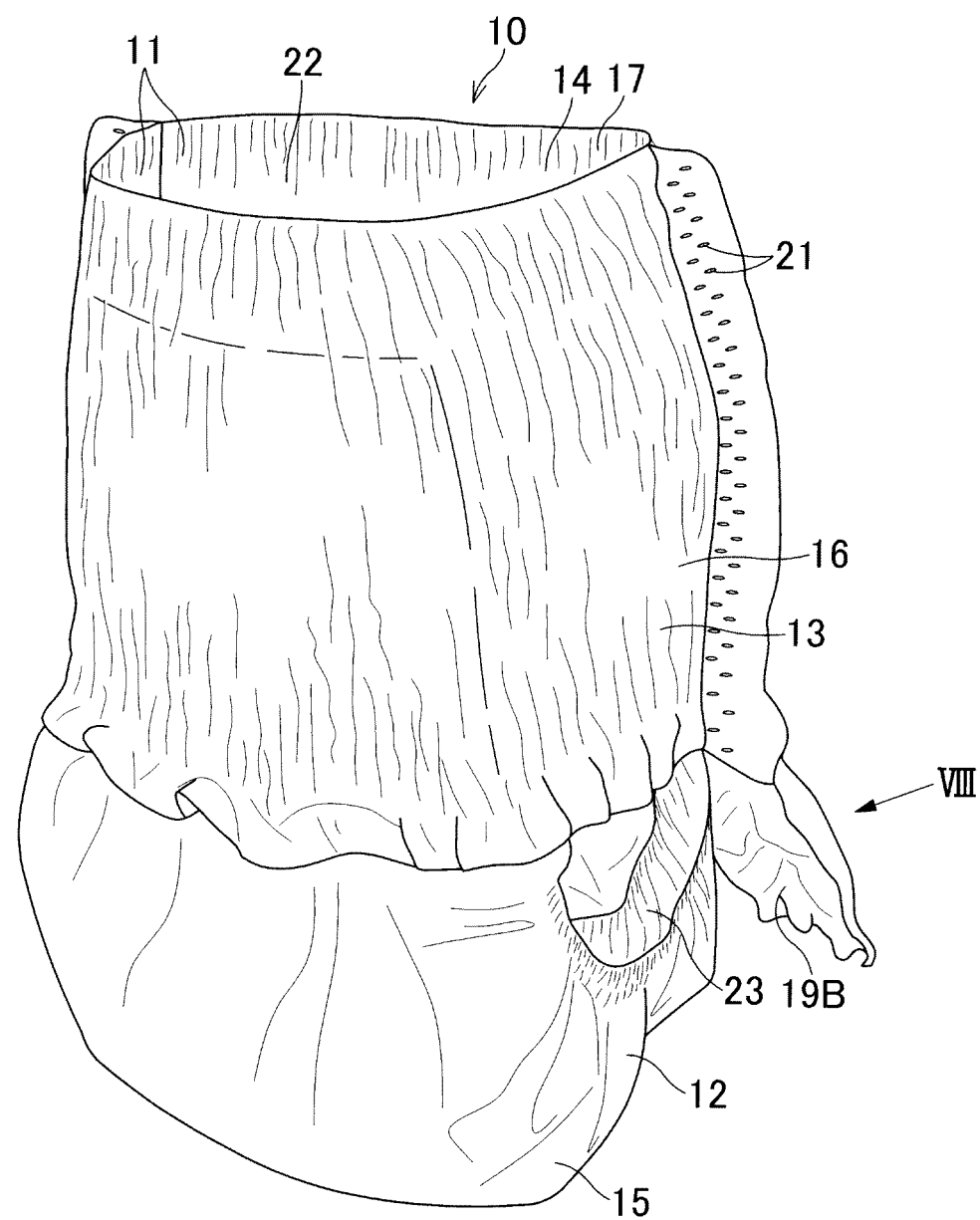
FIG. 1 is a perspective view of a disposable diaper as a first embodiment of the present invention.
Figure 2:
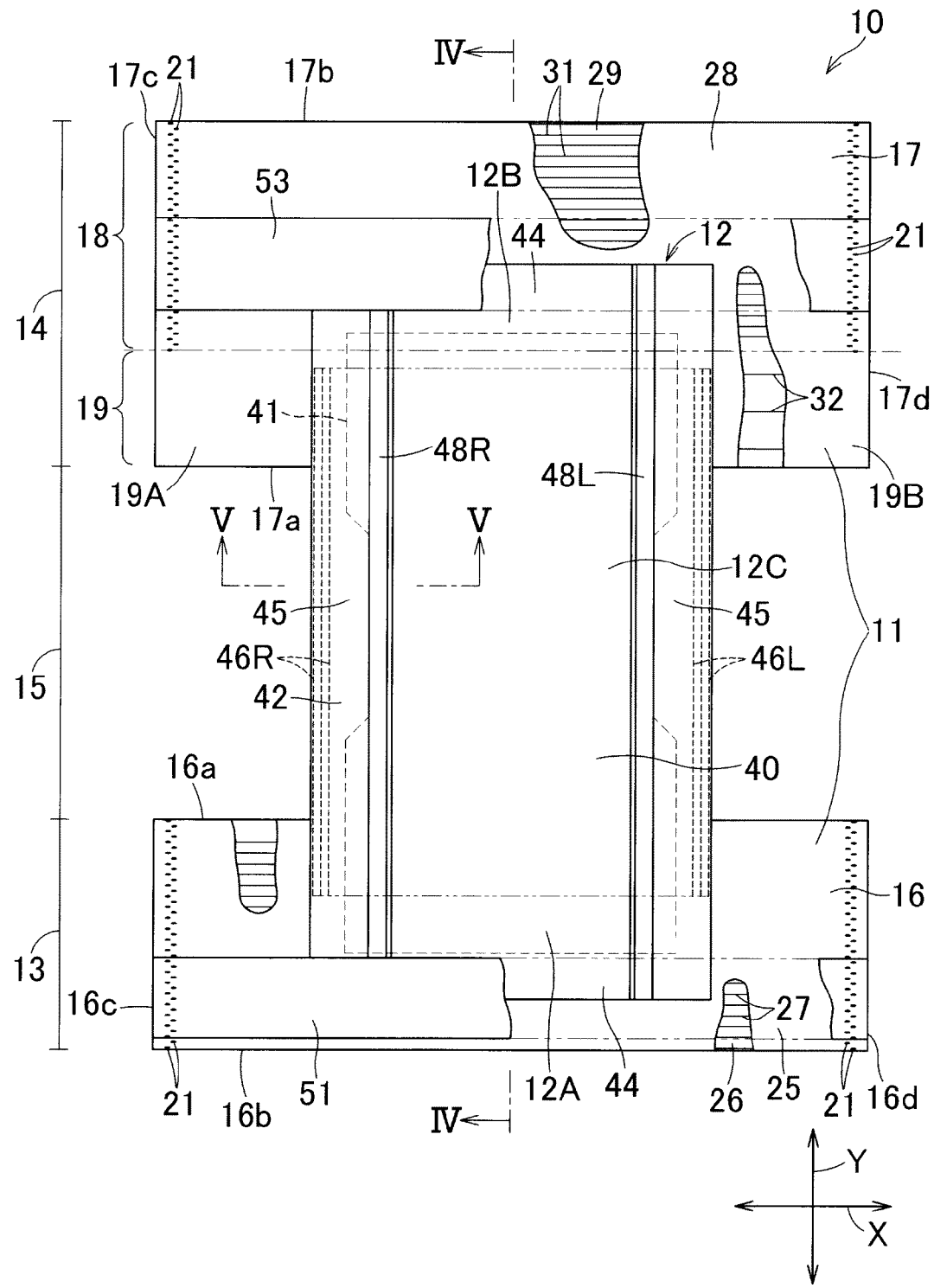
FIG. 2 is a partially cutaway plan view showing the first embodiment of the disposable diaper as has been flatly developed in a front-back direction after front and rear waist regions was peeled off each other at sealed spots and viewed from the inner side of the diaper.

The diaper 10 has a longitudinal direction Y, a transverse direction X orthogonal to the longitudinal direction Y, a skin-facing side and a non-skin-facing side and comprises elastic waist panels 11 and a liquid-absorbent structure 12 attached to the skin-facing side of the elastic waist panel 11 to define a front waist region 13, a rear waist region 14 and a crotch region 15 extending between the front and rear waist regions 13, 14 in the longitudinal direction Y.

The elastic waist panels 11 comprise a front waist panel 16 forming the front waist region 13 and a rear waist panel 17 forming the rear waist region 14.

The front waist panel 16 has a generally rectangular shape which is long in the transverse direction X and contoured by an inner end 16a extending in the transverse direction X to intersect the liquid-absorbent structure 12, an outer end 16b spaced from and opposed to the inner end 16a in the longitudinal direction Y and extending in the transverse direction X and side edges 16c, 16d extending between the inner and outer ends 16a, 16b in the longitudinal direction Y and spaced from and opposed to each other in the transverse direction X.

Similarly to the front waist panel 16, the rear waist panel 17 has a generally rectangular shape which is relatively long in the transverse direction X and contoured by an inner end 17a extending in the transverse direction X to intersect the liquid-absorbent structure 12, an outer end 17b spaced from and opposed to the inner end 17a in the longitudinal direction Y and extending in the transverse direction X and side edges 17c, 17d extending between the inner and outer ends 17a, 17b in the longitudinal direction Y and spaced from and opposed to each other in the transverse direction X. The rear waist panel 17 comprises a rear waist main section 18 adapted to face the wearer's rear waist and a buttocks-covering section 19 extending from the rear waist main section 18 toward the crotch region 15 and adapted to face the wearer's buttocks.

The side edges 16c, 16d of the front waist panel 16 are put flat together with and joined to respective parts (side edges of the rear waist main section 18) of the side edges 17c, 17d of the rear waist panel 17 at seam spots arranged intermittently in the longitudinal direction Y, for example, in zigzag pattern whereupon a waist-opening 22 and a pair of leg-opening 23 are formed (See FIG. 1). For this treatment of joining, various means of joining such as thermal embossing or ultrasonic joining may be used.

The front waist panel 16 comprises a first inner sheet 25 lying on the skin-facing side, a first outer sheet 26 lying on the non-skin-facing side and a plurality of front waist elastic elements 27 which are elastic strings or elastic strands sandwiched between the first inner sheet 25 and the first outer sheet 26 to be spaced one from another by a given distance in the longitudinal direction Y and extending in the transverse direction X. The front waist panel 16 is elastically contractible in the transverse direction X under the front waist elastic elements 27.

The rear waist panel 17 comprises a second inner sheet 28 lying on the skin-facing side, a second outer sheet 29 lying on the non-skin-facing side and a plurality of front waist elastic elements 31 and buttocks-covering section elastic elements 32 which are elastic strings or elastic strands sandwiched between the second inner sheet 28 and the second outer sheet 29 to extend in the transverse direction X.

The rear waist elastic elements 31 are sandwiched between the second inner sheet 28 and the second outer sheet 29 in the rear waist main section 18 and the buttocks-covering section elastic elements 32 are sandwiched between the second inner sheet 28 and the second outer sheet 29 in the buttocks-covering section 19. The buttocks-covering section 19 has its both lateral portions 19A, 19B defined outside the liquid-absorbent structure 12 in the transverse direction X.

The respective elastic elements are formed of synthetic or natural material in the form of strings or strands having rubber elasticity. For example, in the case of diapers for babies, dimensions of respective regions of the diaper depend on the diaper's size L, M or S and, in the case of L-size diapers, a total length of the diaper in the longitudinal direction Y is in a range of 470 to 510 mm, length dimensions of the front waist region 13 and the rear waist main section 18 corresponding to the front waist region 13 in the longitudinal direction Y are in a range of 95 to 125 mm and a length dimension of the buttocks-covering section 19 in the longitudinal direction Y is in a range of 45 to 65 mm. The dimensions of the respective regions will be exemplarily indicated on the assumption that the diaper 10 is of L-size in developed and stretched state.

Figure 6:
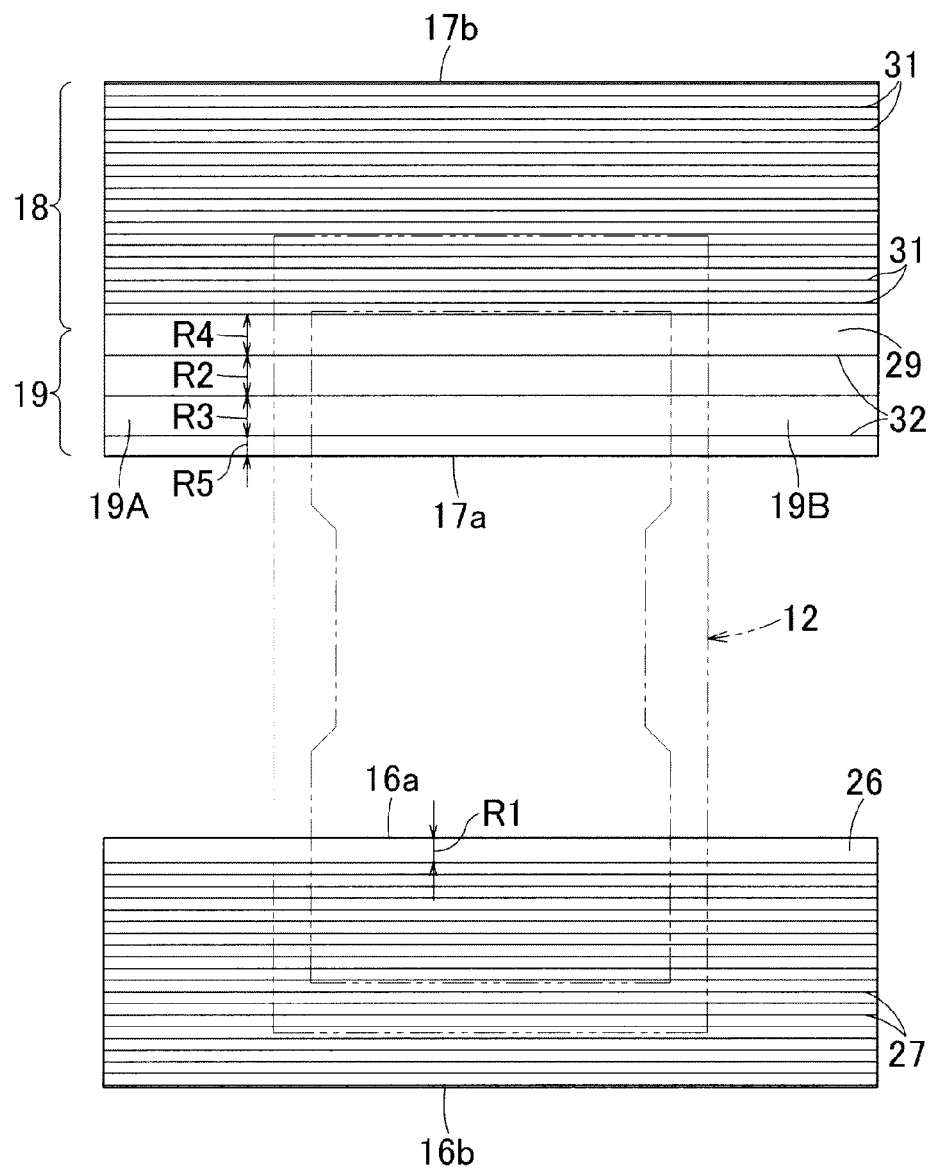
FIG. 6 is a view similar to FIG. 3, showing the flatly developed diaper with the exclusion of a liquid-absorbent structure, first and second inner sheets and first and second fixing sheets.

Referring to FIG. 6, as the front waist elastic elements 27, five elastic elements each having a diameter in range of 450 to 500 dtex and elongation ratio in a range of 2.4 to 2.8 and fifteen elastic elements each having a diameter in a range of 450 to 500 dtex and elongation ratio in a range of 1.8 to 2.4 are located in the vicinity of the outer end 16b of the front waist panel 16. Each pair of the adjacent elastic elements is spaced from each other by a range of 5.0 to 6.0 mm. The front waist elastic element 27 allocated at the lowest position is spaced from the inner end (i.e., the inner end 16a of the front waist panel 16) of the first outer sheet 26 by a dimension R1 in a range of 5 to 20 mm.

As the rear waist elastic elements 31, five elastic elements each having a diameter in range of 450 to 500 dtex and elongation ratio in a range of 2.4 to 2.8 and sixteen elastic elements each having a diameter in a range of 450 to 500 dtex and elongation ratio in a range of 1.8 to 2.4 are provided. Each pair of the adjacent elastic elements is spaced from each other by a range of 5.0 to 6.0 mm.

As the buttocks-covering section elastic elements 32, three elastic elements each having a diameter in a range of 450 to 500 dtex and elongation ratio of 2.2 to 2.6 and each pair of the adjacent elastic elements is spaced from each other by a dimension R2, R3 in a range of 15 to 25 mm. Specifically, the distance dimensions R2, R3 between the adjacent buttocks-covering section elastic elements 32 are triple or more compared to the distance dimensions of both the front waist elastic elements 27 and the rear waist elastic elements 31. A distance dimension R4 between one of the rear waist elastic elements 31 and the adjacent buttocks-covering section elastic element 32 is in a range of 15 to 25 mm and a distance dimension R5 between the buttocks-covering section elastic element 32 which is the nearest to the inner end 17a of the rear waist panel 17 and the inner end (i.e., the inner end 17a of the rear waist panel 17) of the second outer sheet 29 is in a range of 5 to 20 mm.

Referring again to FIGS. 2 through 5, the liquid-absorbent structure 12 has a rectangular shape which is relatively long in the longitudinal direction Y and contoured by front and rear ends extending in the transverse direction X and both side edges extending in the longitudinal direction Y orthogonally to the front and rear ends. The liquid-absorbent structure 12 extends across the crotch region 15 into the front and rear waist regions 13, 14. The liquid-absorbent structure 12 has a front end section 12A lying on the inner surface of the front waist region 13, a rear end section 12B lying on the inner surface of the rear waist region 14 and an intermediate section 12C extending between the front and rear end sections 12A, 12B to define the crotch region 15.

The liquid-absorbent structure 12 preferably comprises a liquid-pervious top-sheet 40 lying on the skin-facing side, a liquid-absorbent core assembly 41 including a liquid-absorbent core formed of a mixture of, for example, fluff pulp fibers and super-absorbent polymer particles wrapped with a liquid-dispersant sheet, and a liquid-impervious cover sheet 42 lying on the non-skin-facing side to cover the outer surface of the liquid-absorbent core assembly 41. The liquid-absorbent core assembly 41 is concave inwardly in the vicinity of its midsection in the longitudinal direction Y to reduce its width dimension. Between the liquid-absorbent core assembly 41 and the cover sheet 42, a liquid-impervious leak-barrier sheet 43 made of plastic material is sandwiched.

The cover sheet 42 extends outward from the peripheral edge of the liquid-absorbent core assembly 41 to define end flaps 44 extending in the transverse direction X outside the respective ends of the liquid-absorbent core assembly 41 opposed to each other in the longitudinal direction Y and side flaps 45 extending in the longitudinal direction Y outside the respective side edges of the liquid-absorbent core assembly 41 opposed to each other in the transverse direction X. The side flaps 45 respectively include two sets of three elastic strands as leg-opening elastic elements 46R, 46L, respectively, which are bonded under tension thereto by hot melt adhesive (not shown). With such arrangement, the side flaps 45 cooperate with the respective leg-opening elastic elements 46R, 46L to function as gasket cuffs kept in close contact around the wearer's thighs.

The lateral portions of the cover sheet 42 respectively defining the side flaps 45 are partially folded inwardly to form a pair of folded regions 48R, 48L extending in the longitudinal direction Y. The respective folded regions 48R, 48L include two of elastic strands as cuff elastic elements 49 attached under tension to respective inner surfaces of these folded regions 48R, 48L by hot melt adhesive (not shown). With the diaper 10 put on the wearer's body, the folded regions 48R, 48L and parts of the respective side flaps 44 are spaced upward from the inner sheet 40 under contraction of the cuff elastic elements 49 to form a pair of gasket cuffs functioning to prevent body waste from sideway leaking from the diaper 10.

As appropriate material for the leg-opening elastic elements 46R, 46L as well as for the cuff elastic elements 49, the materials in the form of strings or strands each having rubber elasticity and a diameter in a range of about 350 to 1240 dtex and a elongation ratio in a range of 2.0 to 3.0 may be used. The adjacent elastic elements are spaced from each other preferably by a distance in a range of 3.0 to 6.0 mm. The number of the leg-opening elastic elements 46R, 46L as well as the number of the cuff elastic elements 49 may be one or two or more so far as the desired tensile force is assured. The other parameters such as a diameter, a distance between each pair of the adjacent elastic elements and a stretch ratio may be appropriately set depending on the number of these elastic elements.

Figure 3:
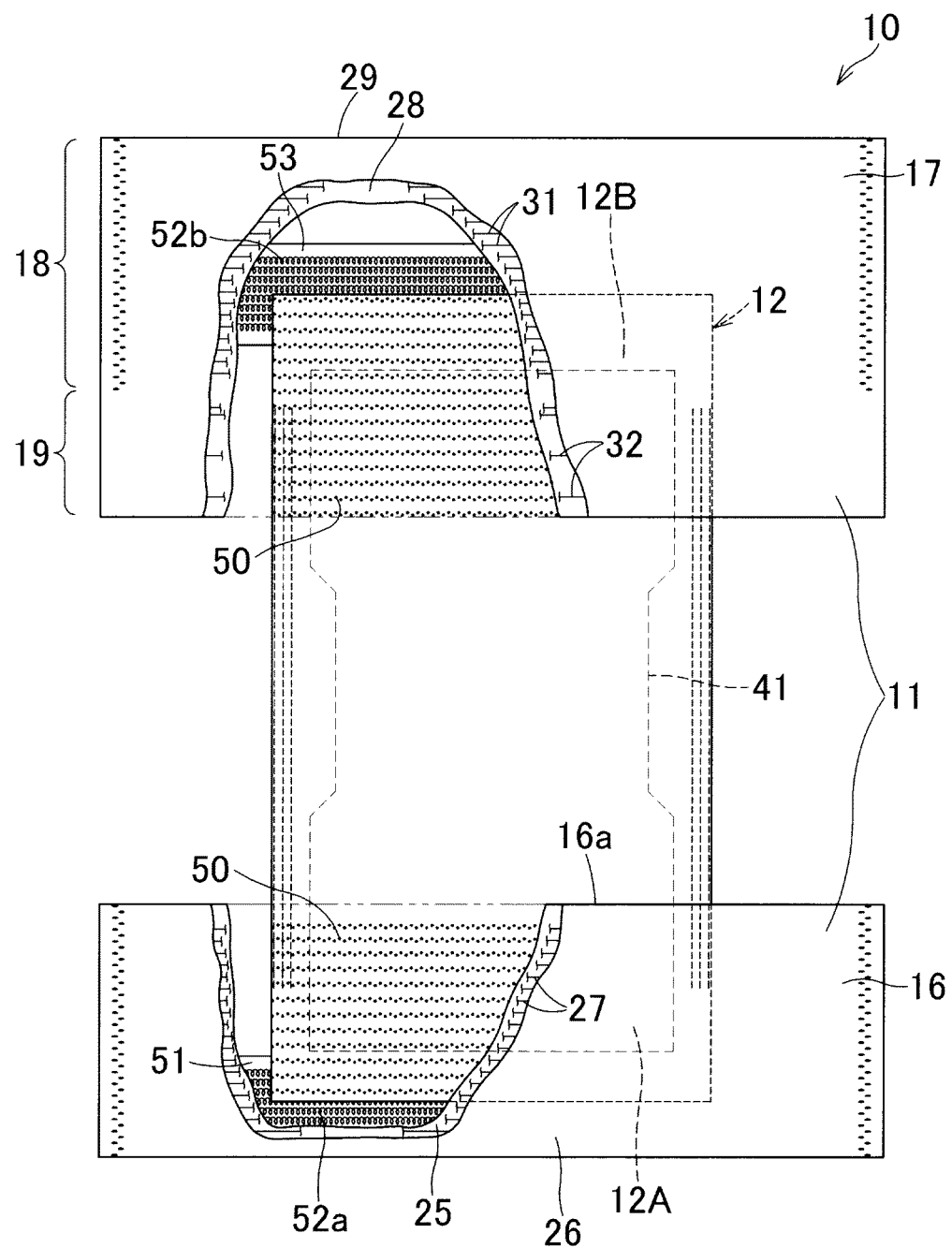
FIG. 3 is a partially cutaway plan view of the diaper in the state shown by FIG. 2 but as viewed from the outer side of the diaper.
Figure 4:
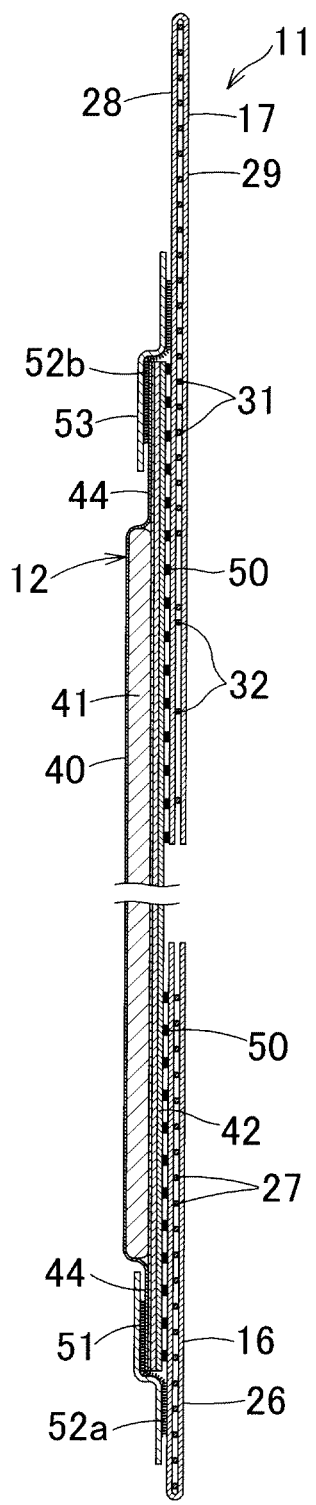
FIG. 4 is a sectional view taken along the line IV-IV in FIG. 2.
Figure 5:
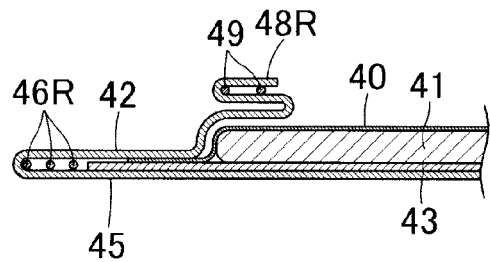
FIG. 5 is a sectional view taken along the line V-V in FIG. 2.

Particularly referring to FIG. 3, the front end section 12A of the liquid-absorbent structure 12 is fixed to the inner surface of the front waist panel 16 by first adhesive 50 applied in a stripe pattern and this inner surface is covered with a first fixing sheet 51 extending in the transverse direction X of the front waist panel 16. The first fixing sheet 51 has its outer surface fixed to the front waist panel 16 and the front end section 12A of the liquid-absorbent structure 12 by hot melt adhesive 52a applied in a pattern of spiral extending in the transverse direction X.

The rear end section 12B of the liquid-absorbent structure 12 is fixed to the inner surface of the rear waist panel 17 by first adhesive 50 applied in a stripe pattern and this inner surface is covered with a second fixing sheet 53 extending in the transverse direction X of the rear waist main section 18. The second fixing sheet 53 has its outer surface fixed to the rear waist panel 17 and the rear end section 12B of the liquid-absorbent structure 12 by hot melt adhesive 52b applied in a pattern of spiral extending in the transverse direction X. The coating pattern of the first adhesive 50 is not limited to the stripe pattern but may include the other various patterns of well known art such as spiral pattern or dotted pattern.

The front waist panel 16 is free from being coated with the first adhesive 50 along the inner end 16a and, in consequence, the region along the inner end 16a has somewhat free skirt when the diaper 10 is seen head-on (See FIG. 1). As will be apparent from FIG. 3, the lowermost one of the front waist elastic elements 27 lies along a boundary between the region coated with the first adhesive 50 and the region not coated with the first adhesive 50. Consequentially, flexible texture of the region not coated with the first adhesive 50 can be maintained.

Figure 7:
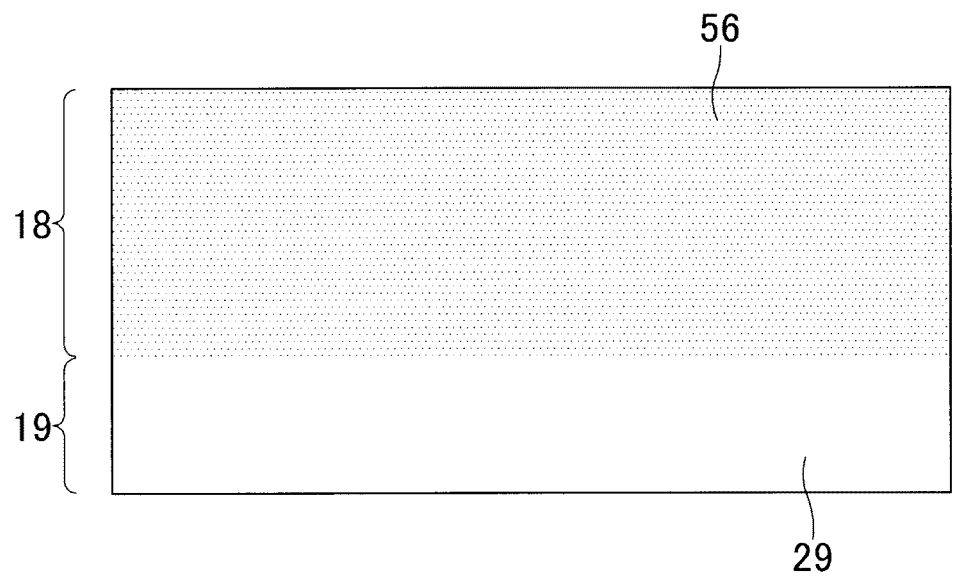
FIGS. 7 (a) and (b) are plan views of respective inner surfaces of first and second outer sheets to illustrate coating patterns of second and third adhesive.
Figure 7:
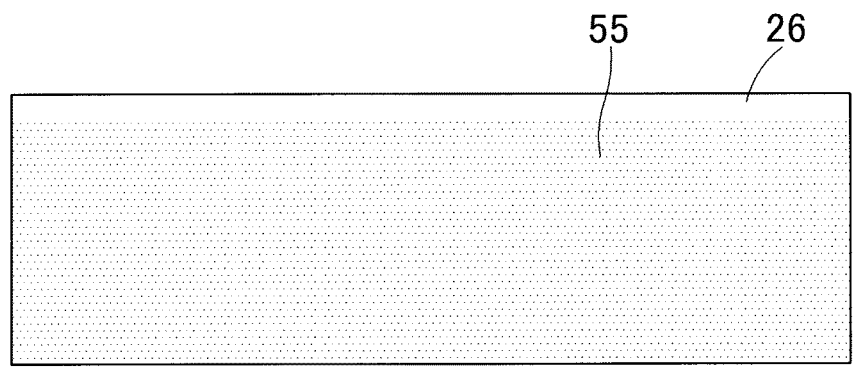

According to one or more embodiment of the present invention, a sheet material is folded into two layers respectively serve as the first inner sheet 25 and the first outer sheet 26 in the front waist panel 16 and the folded line serves as the peripheral edge of the waist-opening 22. The first inner sheet 25 and the first outer sheet are bonded to each other by second adhesive 55 applied to the inner surface of at least one of the first inner sheet 25 and the first outer sheet 26 as shown in FIG. 7 (b). According to the other embodiments, the first inner sheet 25 and the first outer sheet 26 can be provided as two separate sheets.

According to one or more embodiment of the present invention, a sheet material is folded into two layers respectively serve as the second inner sheet 28 and the second outer sheet 29 in the rear waist panel 17 and the folded line serves the peripheral edge of the waist-opening 22. The second inner sheet 25 and the second outer sheet are and bonded to each other by third adhesive 56 applied to the inner surface of at least one of the second inner sheet 28 and the second outer sheet 29 as shown in FIG. 7 (a). Both the front waist panel 16 and the rear waist main section 18 are coated over the entire areas thereof with the second adhesive 55 and third adhesive 56, respectively, and therefore these sheets would not be peeled off in the course of making the diaper 10 and/or during use of the diaper 10. According to the other embodiments, the second inner sheet 28 and the second outer sheet 29 also can be provided as two separate sheets.

Figure 9:
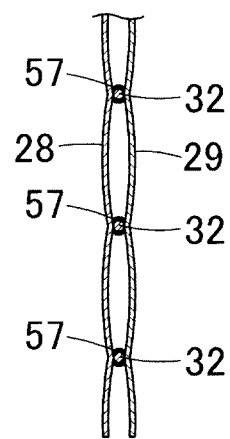
FIG. 9 is a sectional view taken along the line IX-IX in FIG. 8.

As shown in FIG. 7 (a), the third adhesive 56 is not applied to the inner surface of the second outer sheet 29 defining the buttocks-covering section 19 and, in this region, the sheets 28, 29 are bonded to each other only by fourth adhesive 57 applied to peripheral surfaces of the respective buttocks-covering section elastic elements 32 as will be understood from FIG. 9.

As has previously been described, the sheets 28, 29 are bonded to each other only by fourth adhesive 57 applied to peripheral surfaces of the respective buttocks-covering section elastic elements 32 in the buttocks-covering section 19 and the distance dimensions R2, R3 between the adjacent buttocks-covering section elastic elements 32 are triple or more compared to the distance dimensions of both the front waist elastic elements 27 and the rear waist elastic elements 31. As a consequence, the bonded area in the buttocks-covering section 19 is smaller than those in the front waist panel 16 and the rear waist main section 18 and stiffness of the buttocks-covering section 19 is correspondingly low.

Figure 8:
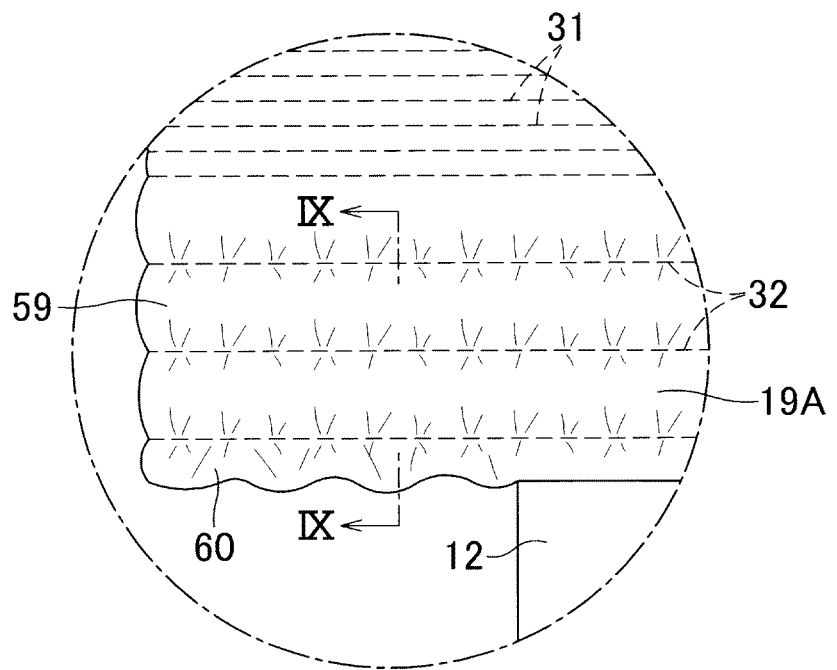
FIG. 8 is a scale-enlarged diagram illustrating a part of buttocks-covering section as viewed in a direction indicated by the arrow VIII in FIG. 1.

Referring to FIG. 8, the lateral section 19A of the buttocks-covering portion 19 has a side edge 59 which is not rectilinear but wavy. Specifically, except the region in which the buttocks-covering section elastic elements are located, the second inner sheet 28 and the second outer sheet 29 are not bonded to each other. With such arrangement, the regions of the sheet member in the vicinity of the ends of the respective buttocks-covering section elastic elements 32 are pulled inward under contraction of these elastic elements 32 while the regions of the sheet member defined between each pair of the adjacent elastic elements 32 respectively describe curves which are convex outward. In the lateral portion 19A of the buttocks-covering section 19, a lower end 60 is not fixed to the liquid-absorbent structure 12 and, in consequence, has a frill-like shape defined by a wavy line. The side edge 59 as well as the lower end 60 of the lateral portion 19A in the buttocks-covering section 19 describing such a wavy curve advantageously prevents the wearer's skin from being irritated when the wearer's skin comes in contact with these regions. In addition, none of the buttocks-covering section elastic elements 32 is arranged along the lower end 60 of the buttocks-covering section 19 and therefore the fourth adhesive 57 would not run off the lower end 60 of the buttocks-covering section 19 and attach to the wearer's skin even if the fourth adhesive 57 runs off the peripheral surfaces of the respective elastic elements 32. It should be appreciated here that, while FIG. 8 is the scale-enlarged diagram illustrating a part of the lateral portion 19A, the lateral portion 19B is constructed in the same manner as the lateral portion 19A.

An application quantity of the second adhesive 55 as well as the third adhesive 56 is in a range of 2.0 to 7.0 g/m². An application quantity of the fourth adhesive 57 per 1 m of the buttocks-covering section elastic element 32 is in a range of 0.03 to 0.07 g/m. The front waist panel 16 and the rear waist main section 18 of the rear waist panel 17 are respectively formed of the inner and outer sheets 25, 26; 28, 29 bonded to each other by the second adhesive 55 and the third adhesive 56 applied to the respective inner surfaces according to the present embodiment. However, it is also possible to bond the inner and outer sheets 25, 26; 28, 29 to each other by the second adhesive 55 applied to peripheral surfaces of the respective front waist elastic elements 27 as in the case of the buttocks-covering section 19 or by the third adhesive 56 applied to peripheral surfaces of the respective rear waist elastic elements 31.

While the various well known types of adhesive conventionally use in the relevant technical field may be selectively used as the first through fourth adhesive 50, 55, 56, 57, rubber-based adhesive such as SBS- or SIS-based adhesive may be preferably used. In addition, while the first through third adhesive 50, 55, 56 is applied in the dotted pattern according to one or more embodiment, it is possible to apply these adhesive in the other various patterns of well known art such as spiral-, wavy- or reticular pattern.

Second Embodiment

Figure 10:
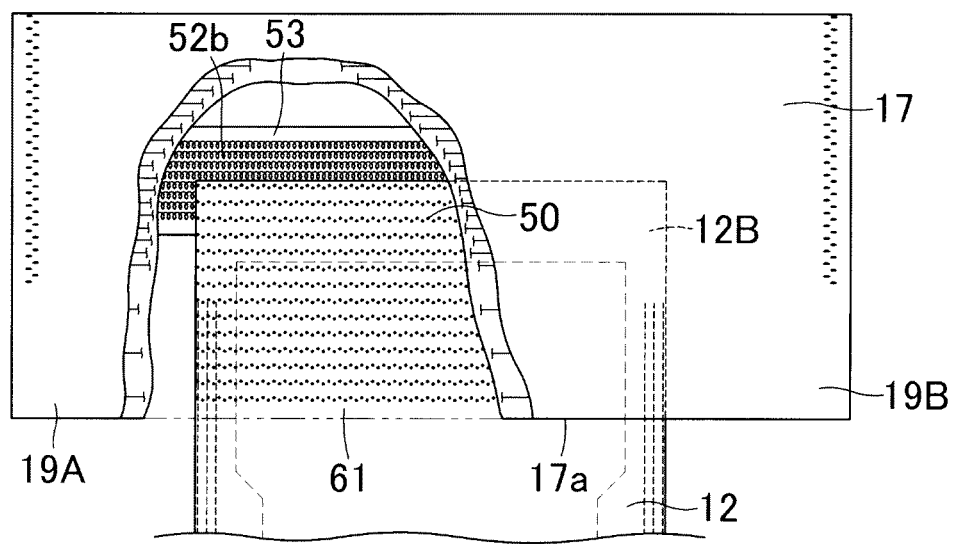
FIG. 10 is a partially cutaway plan view of a rear waist panel in a second embodiment of the diaper according to the present invention as viewed from the outside.
Figure 11:
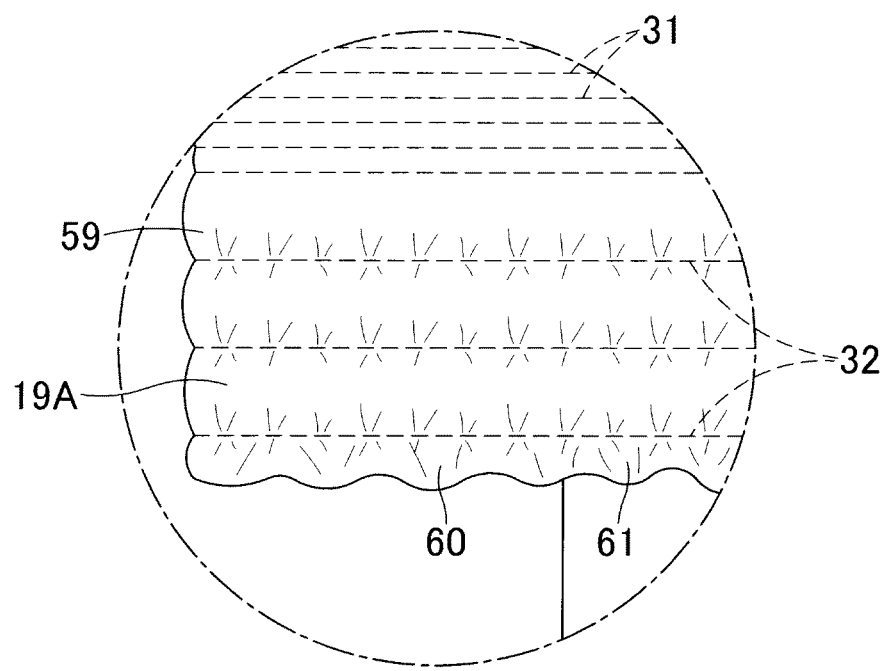
FIG. 11 is a scale-enlarged diagram similar to FIG. 8, illustrating a part of buttocks-covering section in the diaper according to the second embodiment of the present invention.

According to a second embodiment, as will be apparent from FIGS. 10 and 11, in a middle region of the buttocks-covering section 19 facing the rear end section 12B of the liquid-absorbent structure 12, the buttocks-covering section 19 is not coated with the first adhesive 50 along its lower end 61 (corresponding to the inner end 17a of the rear waist panel 17), i.e., not bonded to the liquid-absorbent structure 12. The lower end 61 of the buttocks-covering section 19 left free from the liquid-absorbent structure 12 in this fashion has somewhat skirt and flexible appearance and, in addition, the fourth adhesive 57 would not run off beyond the lower end 61 and uncomfortably irritate the wearer's skin since none of the buttocks-covering section elastic elements 32 is arranged along this lower end 61. The lower end 60 of the lateral portion 19A as well as the lower end 61 of the middle region in the buttocks-covering section 19 continuously extending in the transverse direction X to present such skirt appearance is preferable from a viewpoint of the appearance of the article.

As the respective component members of the diaper 10, in addition to the specific numbers of the specific materials described in this specification, various numbers and various kinds of well known material usually used in the relevant technical field may be selectively used. While the front and rear waist panels 16, 17 are elastic by arranging a plurality of elastic elements thereon, the front and rear waist panels 16, 17 may be formed of sheet materials having elasticity in themselves. It is also possible to replace elastic strings or elastic strands used as the elastic elements by elastic tapes or elastic sheets for the purpose of elastic the front and rear waist panels 16, 17.

Instead of forming the buttocks-covering section 19 to extend continuously from the rear waist main section 18, it is possible to form the buttocks-covering section 19 separately of the rear waist main section 18 or of a sheet material different from the sheet material forming the rear waist main section 18. When the buttocks-covering section 19 is formed of the sheet material different from the sheet material of the rear waist main section 18, the buttocks-covering section 19 is preferably formed of the sheet material having flexibility similar to or higher than flexibility of the sheet material forming the rear waist main section 18.

The aspects of the present invention described above may be arranged in at least following items:

(i) A disposable wearing article (10) having a longitudinal direction (Y), a transverse direction (X) orthogonal to the longitudinal direction, a skin-facing side, a non-skin-facing side, a front waist region (13), a rear waist region (14), a crotch region (15) extending between the front and rear waist regions, and comprising elastic waist panels (11) defining the front and rear waist regions and a liquid-absorbent structure (12) attached to an inner surface of the elastic waist panels to define the crotch region, wherein:

the rear waist region comprises an inner sheet (28) lying on the skin-facing side, an outer sheet (29) lying on the non-skin-facing side, a rear waist main section (18) and a buttocks-covering section (19) lying below the rear waist main section;

the buttocks-covering section includes a plurality of buttocks-covering section elastic elements (32) arranged thereon to extend in the transverse direction at constant intervals in the longitudinal direction; and in the buttocks-covering section, the inner sheet and the outer sheet are bonded to each other by adhesive (57) applied to peripheral surfaces of respective the buttocks-covering section elastic elements.

The aspect of the present invention described in the above item (i) may provide one or more of the following advantageous effects:

(a) According to the present invention, the second inner sheet and the second outer sheet in the buttocks-covering section are bonded to each other by the adhesive applied to peripheral surfaces of the respective buttocks-covering section elastic elements. With this unique arrangement, the desired tensile force is assured but stiffness of the buttocks-covering section as a whole is restricted to a relatively low level and therefore there is no anxiety that the buttocks-covering section might uncomfortably irritate the wearer's skin even if this section comes in contact with the wearer's skin.

Additionally, one or more of the following embodiments are provided in accordance with further aspects:

(ii) The rear waist main section includes a rear waist elastic.

(iii) The rear waist elastic includes a plurality of rear waist elastic elements (31) arranged thereon to extend in the transverse direction at constant intervals in the longitudinal direction and a distance one from another of the buttocks-covering section elastic elements is larger than a distance one from another of the rear waist elastic elements.

(iv) The rear waist elastic is formed of an elastic sheet.

(v) The front waist region comprises an inner sheet lying on the skin-facing side, an outer sheet lying on the non-skin-facing side and a front waist elastic.

(vi) The front waist elastic includes a plurality of front waist elastic elements (27) arranged thereon to extend in the transverse direction at constant intervals in the longitudinal direction.

(vii) The front waist elastic is formed of an elastic sheet.

(viii) The inner sheet (28) and the outer sheet (29) of the rear waist region are formed of a continuous sheet.

(ix) The inner sheet and the outer sheet of the rear waist region are respectively formed of individual sheets.

(x) At least one of the inner sheet and the outer sheet of the rear waist region, a sheet of which the rear waist main section is formed and a sheet of which the buttocks-covering section is formed are individual wherein the sheet of which the buttocks-covering section is formed is more flexible than the sheet of which the rear waist main section is formed.

(xi) In the rear waist main section, the inner sheet and the outer sheet is bonded to each other by adhesive applied on at least one of surfaces thereof facing each other.

(xii) In the rear waist main section, the inner sheet and the outer sheet are bonded to each other by adhesive applied to peripheral surfaces of respective the rear waist elastic.

(xiii) The elastic waist panels comprise a front waist panel (16) defining the front waist region and a rear waist panel (17) defining the rear waist region;

the liquid-absorbent structure is fixed to respective inner surfaces of the front waist panel and the rear waist panel by adhesive (50) applied to a surface of the liquid-absorbent structure opposed to the inner surfaces; and, of inner ends (17a) of the front and rear panels, at least a region of the liquid-absorbent structure facing the inner end of the rear waist panel is free from being coated with the adhesive.

According to the embodiments in the above (ii) to (xiii), the advantageous effect(s) set forth at (a) is/are better ensured. Further advantageous effects of the respective embodiments may be obtained as discussed in the respective related descriptions.

As used herein, terms "first", "second", "third" and "fourth" are use merely for distinguishing between similar elements.

The invention claimed is:

1. A disposable wearing article comprising:
a longitudinal direction;
a transverse direction orthogonal to said longitudinal direction;
a skin-facing side;
a non-skin-facing side;
a front waist region;
a rear waist region;
a crotch region extending between said front and rear waist regions;
elastic waist panels defining said front and rear waist regions; and
a liquid-absorbent structure attached to an inner surface of said elastic waist panels to define said crotch region,
said rear waist region comprises an inner sheet lying on said skin-facing side, an outer sheet lying on said non-skin-facing side, a rear waist main section and a buttocks-covering section lying below said rear waist main section;
said buttocks-covering section includes a plurality of buttocks-covering section elastic elements arranged thereon to extend in said transverse direction at constant intervals in said longitudinal direction;
in said buttocks-covering section, said inner sheet and said outer sheet are bonded to each other only by adhesive applied to peripheral surfaces of respective said buttocks-covering section elastic elements;
said rear waist main section includes rear waist elastic;
said rear waist elastic includes a plurality of rear waist elastic elements arranged thereon to extend in said transverse direction at constant intervals in said longitudinal direction and a distance one from another of said buttocks-covering section elastic elements is larger than a distance one from another of said rear waist elastic elements; and
a shortest distance between said rear waist elastic element and said buttocks-covering section elastic element is the same as said distance one from another of said buttocks-covering section elastic elements,
wherein
in said rear waist main section, said inner sheet and said outer sheet is bonded to each other by adhesive applied on at least one of surfaces thereof facing each other.

2. The wearing article defined by claim 1, wherein said front waist region comprises an inner sheet lying on said skin-facing side, an outer sheet lying on said non-skin-facing side and a front waist elastic.

3. The wearing article defined by claim 2, wherein said front waist elastic includes a plurality of front waist elastic elements arranged thereon to extend in said transverse direction at constant intervals in said longitudinal direction.

4. The wearing article defined by claim 2, wherein said front waist elastic is formed of an elastic sheet.

5. The wearing article defined by claim 1, wherein said inner sheet and said outer sheet of said rear waist region are formed of a continuous sheet.

6. The wearing article defined by claim 1, wherein said inner sheet and said outer sheet of said rear waist region are respectively formed of individual sheets.

7. The wearing article defined by claim 1, wherein of at least one of said inner sheet and said outer sheet of said rear waist region, a sheet of which said rear waist main section is formed and a sheet of which said buttocks-covering section is formed are individual wherein said sheet of which said buttocks-covering section is formed is more flexible than said sheet of which said rear waist main section is formed.

8. The wearing article defined by claim 1, wherein in said rear waist main section, said inner sheet and said outer sheet are bonded to each other by adhesive applied to peripheral surfaces of respective said rear waist elastic.

9. The wearing article defined by claim 1, wherein:
said elastic waist panels comprise a front waist panel defining said front waist region and a rear waist panel defining said rear waist region;
said liquid-absorbent structure is fixed to respective inner surfaces of said front waist panel and said rear waist panel by adhesive applied to a surface of said liquid-absorbent structure opposed to said inner surfaces; and,
of inner ends of said front and rear waist panels, at least a region of said liquid-absorbent structure facing said inner end of said rear waist panel is free from being coated with said adhesive.

* * * * *